US009835638B2

(12) United States Patent
Bucher et al.

(10) Patent No.: US 9,835,638 B2
(45) Date of Patent: Dec. 5, 2017

(54) DEVICE FOR GRIPPING VESSELS (71) Applicant: Roche Diagnostics Operations, Inc., Indianapolis, IN (US)

(72) Inventors: Marco Bucher, Hohenrain (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/561,314

(22) Filed: Dec. 5, 2014

(65) Prior Publication Data
US 2015/0160250 A1    Jun. 11, 2015

(30) Foreign Application Priority Data

Dec. 10, 2013 (EP) .................... 13196487

(51) Int. Cl.
*G01N 35/04* (2006.01)
*G01N 35/00* (2006.01)

(52) U.S. Cl.
CPC . *G01N 35/0099* (2013.01); *G01N 2035/0406* (2013.01); *G01N 2035/0484* (2013.01); *Y10T 436/114165* (2015.01)

(58) Field of Classification Search
CPC ............... G01N 35/0099; G01N 35/00; G01N 2035/0406; G01N 2035/0484; G01N 2035/0401; G01N 2035/04; G01N 2035/02; G01N 2035/0482; G01N 2035/0474; Y10T 436/00; Y10T 436/11; Y10T 436/114165; Y10T 436/113332
USPC ............................................. 436/48, 47, 43
See application file for complete search history.

(56) References Cited

U.S. PATENT DOCUMENTS

| 5,337,919 | A | * | 8/1994 | Spaulding | B65G 1/1373 221/127 |
| 6,036,812 | A | * | 3/2000 | Williams | B65G 1/045 156/277 |
| 7,175,381 | B2 | * | 2/2007 | Guerra | B25J 9/109 414/744.5 |

FOREIGN PATENT DOCUMENTS

| EP | 1854589 A1 | 11/2007 |
| WO | 2007/039524 A3 | 4/2007 |
| WO | 2008/078304 A3 | 7/2008 |
| WO | 2012/123566 A1 | 9/2012 |

* cited by examiner

*Primary Examiner* — Christine Y Mui
(74) *Attorney, Agent, or Firm* — Roche Diagnostics Operations, Inc.

(57) ABSTRACT

A device for gripping vessels is presented. The device comprises a mount, a support having a longitudinal axis coupled to the mount so to be rotatable relative to the mount around the longitudinal axis, a rotating mechanism for rotating the support, a gripper coupled to the support so to be translatable relative to the support along the longitudinal axis. The gripper has jaws for gripping a vessel, a translating mechanism for translating the gripper, at least one actuator for driving the translating mechanism and/or rotating mechanism and at least two reference elements fixed to the mount in at least two different stop positions. The jaws are passively biasable towards each other for holding a vessel in positions other than the at least two stop positions. The jaws are actively biasable away from each other by pushing the gripper against a reference element in one of the stop positions.

13 Claims, 9 Drawing Sheets

DEVICE FOR GRIPPING VESSELS

CROSS-REFERENCE TO RELATED APPLICATIONS

This application is a continuation of EP 13196487.6, filed Dec. 10, 2013, which is hereby incorporated by reference.

BACKGROUND

The present disclosure generally relates to the field of biochemical research, biochemical routine analytics, clinical diagnostics and clinical research and, in particular, to a device for gripping vessels, for example, for transferring vessels to an analytical compartment for analyzing samples.

In recent years, automated analytical instruments ("analyzers") offering a variety of analytical methods have become commercially available. Modern analyzers usually can process samples in standard sample vessels such as plastic cuvettes which allow for an easy and cost-effective sample analysis such as, for example, by photometric methods. In order to process samples in a batch-wise or continuous manner, it is known to supply vessels in bulk form to the analyzer which are automatically separated to provide single (separated) vessels for the processing of samples. An apparatus for the automated separation of vessels supplied in bulk form to an analytical instrument is known in the art.

For using vessels in the process of analyzing samples, the vessels are transported from a picking position of the apparatus for the automated separation of vessels to an analytical compartment. It is known to transport vessels by an automated gripper configured to grip a vessel at the picking position and release the vessel at another position. In conventional analyzers, such a gripper is provided with two gripping jaws for gripping or releasing of a vessel which are coupled to a separate motor controllable to move the gripping jaws towards or away from each other. Such gripper, for example, can be found in commercially available analyzers.

However, there is a need for an improved device for gripping vessels which is simple and robust in construction, which can be manufactured and maintained in cost-efficient manner where device control is less complex than conventional devices resulting in a reduced risk of failure and false operations and that requires only a comparably small constructional space.

SUMMARY

According to the present disclosure, a device, system and method for gripping vessels are presented. The device can comprise a stationary mount, an elongate support having a longitudinal axis coupled to the mount in a manner to be rotatable relative to the mount around the longitudinal axis, a rotating mechanism for rotating the support, and a gripper coupled to the support so to be translatable relative to the support along the longitudinal axis. The gripper can be provided with gripping jaws for gripping a vessel. The device can further comprise a translating mechanism for translating the gripper, a first actuator for driving the rotating mechanism. a second actuator for driving the translating mechanism, and at least two reference elements fixed to the mount in at least two different stop positions. The gripping jaws can be passively biasable towards each other for holding a vessel at positions other than the at least two stop positions. The gripping jaws can be actively biasable away from each other by pushing the gripper against a reference element in one of the stop positions.

Accordingly, it is a feature of the embodiments of the present disclosure to provide for an improved device for gripping vessels which is simple and robust in construction, which can be manufactured and maintained in cost-efficient manner where device control is less complex than conventional devices resulting in a reduced risk of failure and false operations and that requires only a comparably small constructional space. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used herein, the term "vessel" can indicate any container capable of receiving a liquid. In one embodiment, the vessel can be a cuvette. In one embodiment, the vessel can comprise a body at least in part optically transparent to receive liquids in an inner space and to allow the photometric measurement of a liquid sample contained therein, i.e. the measurement of changes in optical transmission, such as absorbance or scattering, used in the optical analysis of analytes present in a sample. The vessel may, for example, be used in the performance of scattering assays to detect the result of a chemical or biological reaction or to monitor the progress of a chemical or biological reaction such as, for example, in a coagulation assay, agglutination assay and turbidimetric assay. In one embodiment, the body of the vessel can comprise side walls, a closed bottom and an upper opening for allowing liquids to be introduced in the inner space formed by the side walls and the closed bottom. In one embodiment, the vessel can comprise a flange projecting outwards from the body so that the vessel can be gripped at the flange by a gripper. The flange can, for example, be arranged in proximity to the upper opening. In one embodiment, the vessel can have two plane-parallel walls wherein at least one wall can be provided with the flange projecting from the wall. In one embodiment, the flange can project perpendicularly from the body. In one embodiment, the flange can be integrally formed with the wall it is projecting from. In one embodiment, the flange can be provided with at least one engagement element such as, but not limited to, a depression or a projection, for interacting with another engagement element provided by the gripper. The above-described various embodiments of the vessel can be used alone or in any combination thereof.

A new device for gripping vessels is proposed. In one embodiment, the device for gripping vessels can comprise a stationary mount. In one embodiment, the device for gripping vessels can comprise an elongate support having a longitudinal axis which can be coupled to the mount as to be rotatable relative to the mount around the longitudinal axis. In one embodiment, the elongate support can have a vertical orientation. In one embodiment, the elongate support can have a horizontal orientation. In one embodiment, the elongate support can be inclined with respect to the vertical or horizontal orientation. In one embodiment, the support can be provided with a gripper guide extending along the longitudinal axis for guiding a gripper for gripping vessels.

In one embodiment, the device can comprise a gripper coupled to the support as to be translatable relative to the support along the longitudinal axis of the support. In one embodiment, the gripper can be guidable (guided) by the gripper guide which can enable an easy control of the translational movement of the gripper. The gripper can be provided with (for example, two) gripping jaws which can be moved towards each other for gripping a vessel or away from each other for releasing a gripped vessel. By moving the gripping jaws towards each other, the gripper can be brought in a closed condition in which a vessel can be taken up to be held by the gripping jaws. By moving the gripping jaws away from each other, the gripper can be brought in an open condition in which a grasped vessel can be released. In a closed condition, the gripping jaws may not be in contact (i.e. can be spaced with respect to each other). In one embodiment, the gripping jaws can be movable in vertical direction towards or away from each other. In one embodiment, the gripping jaws can be movable in horizontal direction towards or away from each other. In one embodiment, the gripping jaws can be movable in a direction towards or away from each other which can be inclined with respect to the vertical direction or horizontal direction.

In one embodiment, the device can comprise a rotating mechanism for rotating the support around the stationary mount so that the gripper can be rotated around the mount.

In one embodiment, the device can comprise a translating mechanism for translating the gripper along the longitudinal axis of the support, for example, guided by the gripper guide.

In one embodiment, the device for gripping vessels can comprise a first actuator, such as a motor, for driving the rotating mechanism and a second actuator, such as a motor, for driving the translating mechanism. Accordingly, the gripper can be rotated by rotating the support around the mount and/or can be translated along the longitudinal axis. The translating and rotating mechanisms can be driven independently from each other so as to perform a rotational and/or translational movement of the gripper.

In one embodiment, the device can comprise at least two reference elements fixed to the stationary mount in at least two different stop positions. In one embodiment, the at least two reference elements can be fixed to the stationary mount in at least two different stop positions relative to the longitudinal axis. In one embodiment, the at least two reference elements can be fixed to the stationary mount in at least two different stop positions relative to at least two angular positions of a same position with respect to the longitudinal axis. The gripping jaws can be passively biasable (biased) towards each other for holding a vessel in positions relative to the longitudinal axis other than the stop positions, for example, between the at least two stop positions, and the gripping jaws can be actively biasable (biased) away from each other by pushing the gripper against a reference element in one of the stop positions.

Accordingly, the gripping jaws can hold a vessel in positions other than the stop positions which, for example, can be achieved by the resilient (elastic) force of at least one resilient (elastic) element coupled to at least one gripping jaw. By translating the gripper along the longitudinal axis and/or by rotating the gripper around the longitudinal axis, the gripper can be pushed against a reference element so as to move the gripping jaws away from each other for releasing a vessel or for gripping a vessel. As a result, a vessel can be gripped or released in a stop position or can be hold and transported by the gripper in positions other than the stop positions, for example, between the at least two stop positions.

As used herein, the term "passively biasable" can relate to biasing the gripping jaws towards each other without pushing the gripper against a reference element in a stop position. Passive biasing of the gripping jaws, for example, can be achieved by the resilient force of at least one resilient element coupled to at least one gripping jaw. The term "actively biasable" can relate to moving the gripping jaws away from each other by pushing the gripper against a reference element, with the gripping jaws being biased, for example, by counteracting the resilient force of at least one resilient element passively biasing the gripping jaws.

Accordingly, a vessel can be taken up by moving the gripper to a reference element corresponding to a picking position of a vessel, pushing the gripper against the reference element for opening the gripper and moving the gripper away from the stop position so as to close the gripper and grip the vessel. The gripped vessel can be released by moving the gripper to a reference element corresponding to a releasing position of the vessel and pushing the gripper against the reference element for actively opening the gripper and releasing the vessel. As a result, vessels can be taken up and released according to the specific demands of the user.

As described, the gripper can be brought in an opened or closed condition without using a motor for operating the gripping jaws. Instead, the gripper can be opened or closed by translating and/or rotating the gripper and pushing the gripper against a reference element. In one embodiment, the gripper can be opened or closed by translating the gripper along the gripper guide. As the gripper can be operated mechanically, there can advantageously be no need to provide for additional electric wiring to operate the gripper. As a result, the setup of the device can be comparably simple and robust in construction and suitable for long-term maintenance-free usage. Moreover, the device can be highly compact in design resulting in a small foot-print. The device can have few components enabling a low-cost and easy production. As a result, the process of analyzing samples involving the use of sample vessels can be facilitated and performed in a cost-efficient manner.

In one embodiment, the gripper can comprise a gripper head and a gripper base, with the gripper head coupled to the support as to be translatable with respect to the support along the longitudinal axis. In one embodiment, the gripper head can be guidable (guided) by the gripper guide of the support. The gripper head can be coupled to the gripper base in a manner to be movable relative to the gripper base against the resilient force of at least one resilient member by pushing the gripper base against a reference element in a stop position. The gripping jaws can be movably fixed to the gripper base in a manner to be moved together with the gripper base and can be movable towards and away from each other. Furthermore, the gripping jaws can be coupled to the gripper head as to be moved away from each other by pushing the gripper base against a reference element and to be moved towards each other in positions other than the stop positions, for example, between the at least two stop positions. Accordingly, the gripper can readily be opened by pushing the gripper base against a reference element at a stop position and can be closed by the resilient force of the at least one resilient element in positions other than a stop position. This embodiment enables an easy, robust and cost-effective manufacturing of the device.

In one embodiment, the gripper head can be coupled to the gripper base as to be movable relative to the gripper base having a component of movement perpendicular to the longitudinal axis of the support. In one embodiment, the gripper head can be provided with a (e.g. linear) base guide for guiding the gripper base, with the base guide inclined with respect to the longitudinal axis of the support. In one embodiment, the (e.g. linear) base guide can be upwardly inclined with respect to a direction given by the movement of the gripper base triggered by pushing the gripper base against a reference element. Accordingly, when moving the gripper base relative to the gripper head, the gripping jaws can be moved together with the gripper base so as to have a component of movement perpendicular to the longitudinal axis (towards or away from the longitudinal axis). The movement of the gripping jaws perpendicular to the longitudinal axis of the support can advantageously be used to move the gripping jaws towards or away from each other to reach out and grip a vessel. Furthermore, the forward and backward movement of the gripping jaws can advantageously be used for gripping or releasing a vessel.

In one embodiment, the gripper head can be provided with at least one jaw guide coupled to a gripping jaw for guiding the gripping jaw, with the jaw guide shaped as to move the gripping jaws away from each other by pushing the gripper base against a reference element or to move the gripping jaws towards each other between the stop positions. Accordingly, the gripping jaws can readily be moved towards or away from other in an easy, robust and cost-effective manner. In one embodiment, the gripper head can be provided with at least two jaw guides, coupled to the gripping jaws for guiding the gripping jaws, with the jaw guides shaped as to move the gripping jaws away from each other by pushing the gripper base against a reference element or to move the gripping jaws towards each other in positions other than a stop positions, for example, between the at least two stop positions. Accordingly, the gripper can readily be opened or closed in a highly effective manner.

As used herein, the term "stop position" can generally relate to a position of the gripper in which the gripper can have contact with a reference element so as to open or close the gripping jaws. A stop position can relate to a position of the gripper in which the gripper base has contact with a reference element, with the gripper head movable relative to the gripper base. Accordingly, the stop position can comprise a range of positions of the gripper head relative to the longitudinal axis in which the position of the gripper base in contact with a reference element can be unchanged relative to the longitudinal axis.

In one embodiment, the device for gripping vessels can comprise plural reference elements arranged in one stop position relative to the longitudinal axis of the support. Accordingly, the gripper can advantageously be opened in different angular (rotational) positions around the longitudinal axis of a same stop position for taking up or releasing vessels which increases the operational capabilities of the device. In one embodiment, the device for gripping vessels can comprise at least three reference elements arranged in at least three stop positions different with respect to each other. Accordingly, the gripper can advantageously be used to take up a vessel in one stop position and selectively release the vessel at one of a plurality of stop positions which can increase the operational capabilities of the device.

In one embodiment, at least one reference element can be shaped as a ring segment. Accordingly, at a same stop position, a (e.g. broad) range of rotational positions of the gripper around the longitudinal axis can be accessible for up-taking or releasing vessels. The ring segment can be used to keep the gripper in an open position while moving the gripper base along the ring segment. As a result, the gripping jaws can be moved sideways in an open position to a position where a vessel is located, followed by a translation of the gripper head relative to the gripper base so as to close the gripping jaws and grip the vessel. By the reverse operation, the vessel can be released.

In one embodiment, at least one reference element can comprise a guiding face for guiding the gripper. The guiding face can be used to keep the gripper open while moving the gripper along the guiding face in contact with the guiding face by rotating the gripper around the rotational axis. Accordingly, the gripper can readily be kept open in a (e.g. broad) range of rotational positions while guiding the gripper along the guiding face. In one embodiment, the guiding face can be configured as sliding face for sliding engagement with the gripper.

In one embodiment, the gripper can comprise at least one contact wheel, such as, but not limited to an idle roller for rolling on the guiding face of a reference element by rotating the gripper around the longitudinal axis of the support. Accordingly, a frictional force between the gripper and the reference element can advantageously be reduced. In one embodiment, the gripper base can be provided with the wheel.

In one embodiment, the support can be in a vertical position, with the at least two stop positions arranged at different heights. As a result, vessels can be taken up and released in different heights which can be advantageous in analyzers involving the transport of vessels between different heights.

In one embodiment, the translating mechanism and/or the rotating mechanism can be configured as a belt drive which can enable a simple, robust and cost-effective driving of the gripper.

In one embodiment, at least one gripping jaw can comprise at least one engagement element, such as, but not limited to a depression or projection, for engagement with a corresponding engagement element formed by the flange of a vessel. In one embodiment, the flange of the vessel can be provided with at least one depression for engagement with projections formed by the gripping jaw. Accordingly, vessels can be gripped in a more reliable manner so as to reduce the risk of gripping or holding failures.

In one embodiment, the device can comprise a controller, setup to control the translating mechanism and/or rotating mechanism as to move the gripper to a first stop position, opening the gripper by pushing the gripper against a first reference element for taking a vessel up, reclosing the gripper by translating the gripper away from the first reference element so as to grip a vessel, moving the gripper to a second stop position and opening the gripper by pushing the gripper against a second reference element for releasing the vessel. In one embodiment, the controller can be setup to control the translating mechanism and/or rotating mechanism so as to translate and/or rotate the gripper for gripping and releasing a vessel.

A new system, or instrument, for analyzing samples is proposed. The system can be configured to analyze samples with respect to one or more analytical methods, such as, but not limited to, photometric methods such as, for example, photometric measurement in vessels. The system can comprise a separator for separating vessels supplied in bulk form to the separator and providing single vessels to a picking position. As used herein, the term "bulk form" can describe a disordered state of a plurality of vessels, for example, present in a cluster. Vessels in bulk form can be separated (individualized) and delivered separately for the processing of samples. The system can further comprise at least one analytical compartment for analyzing samples. The system can yet further comprise an device for gripping vessels according to one or more of the above-described embodiments for transferring vessels from the picking position located in correspondence to a first stop position to the at least one analytical compartment located in correspondence to at least one second stop position. In one embodiment, the device for gripping vessels can comprise a third stop position for releasing vessels into a waste compartment.

A new process for gripping vessels is proposed. The process can comprise the following: moving a gripper provided with gripping jaws passively biased towards each other to a first stop position, opening the gripper by pushing the gripper against a first reference element for taking up a vessel, reclosing the gripper by moving the gripper away from the first reference element so as to grip a vessel, moving the gripper to a second stop position and opening the gripper by pushing the gripper against a second reference element for releasing the vessel. In one embodiment, moving of the gripper can comprise translating and/or rotating the gripper.

Figure 1:
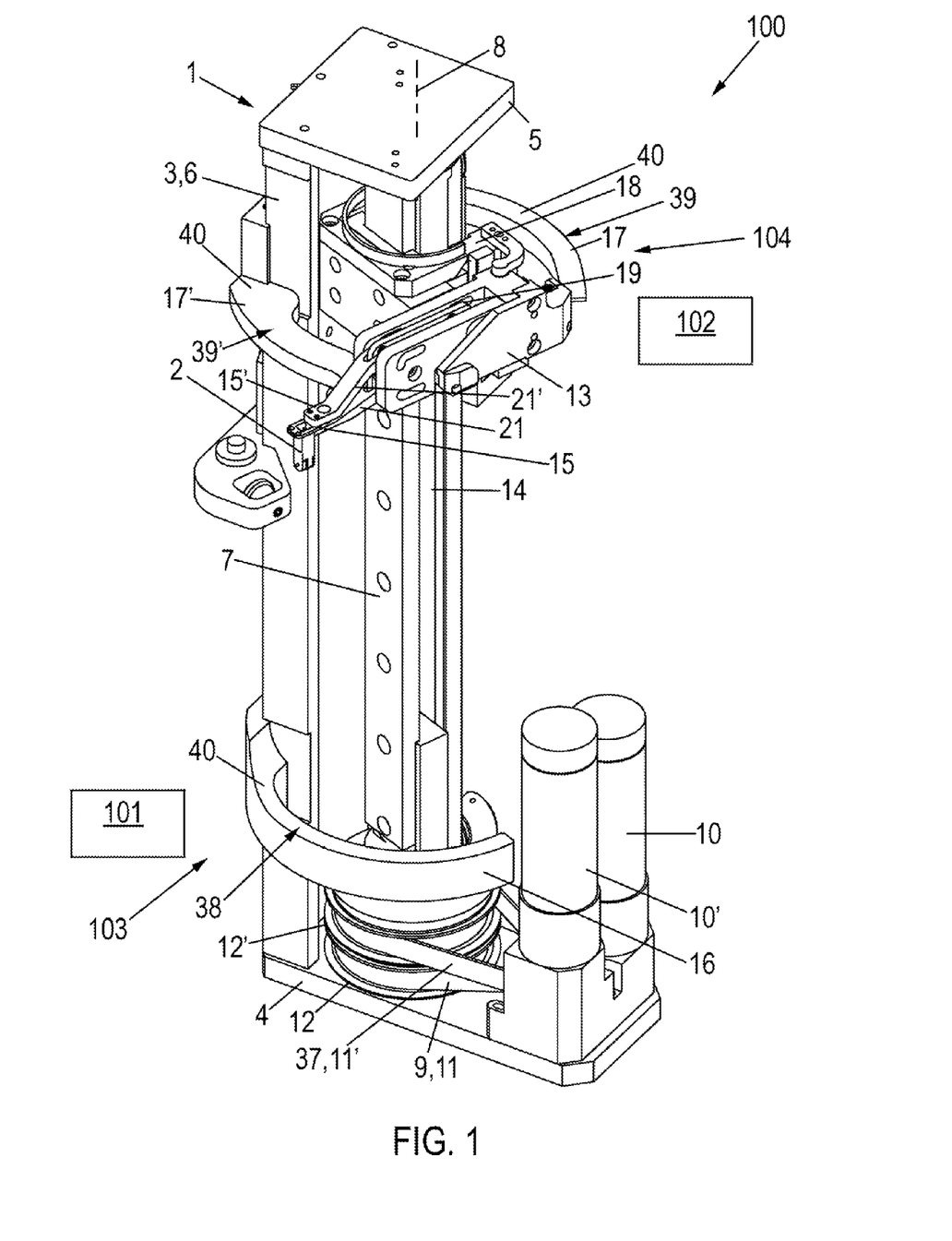
FIG. 1 illustrates a perspective view of an exemplary device for gripping vessels according to an embodiment of the present disclosure.

Referring initially to FIG. 1, an exemplary device 1 for gripping vessels 2 is presented. As schematically illustrated in FIG. 1, the device 1 can, for example, be part of a system, or instrument, for processing samples, generally referred to as reference numeral 100, such as an analytical system for processing samples by one or more analytical methods such as, but not limited to, photometric methods, involving the use of vessels, such as, but not limited to cuvettes. The device 1 for gripping vessels 2 can comprise a stationary mount 3 having a bottom plate 4, a top plate 5 and a vertical beam 6, with the beam 6 fixed to the bottom plate 4 and the top plate 5 fixed to the beam 6.

The device 1 can further comprise an elongate vertical support 7 having a longitudinal axis 8 which can be rotatably fixed to the mount 3. The vertical support 7 can be rotatably fixed to both the bottom plate 4 and the top plate 5 by rotational bearings so as to be rotatable around the longitudinal axis 8.

A rotating mechanism 9 can be coupled to the support 7 for rotating the support 7 around the longitudinal axis 8. The rotating mechanism 9 can be configured as a belt drive comprising an electric motor 10 for driving a belt 11. In one embodiment, the belt 11 can be wound around a driving wheel 12 fixed in rotation to the support 7 so that the support 7 can be rotated together with the wheel 12 which can be rotated by the motor-driven belt 11.

Figure 3:
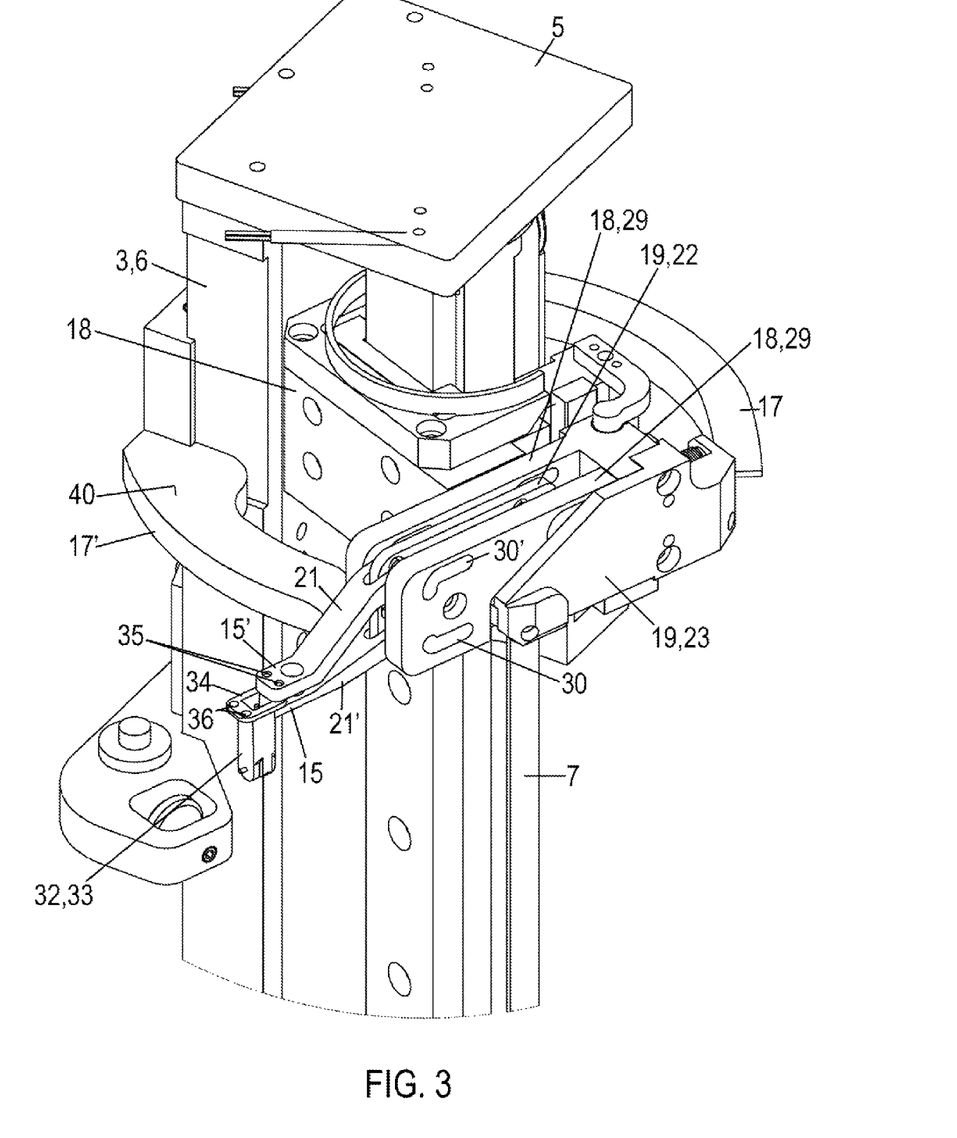
FIG. 3 illustrates an enlarged detail (upper portion) of the device of FIG. 1 according to an embodiment of the present disclosure.
Figure 4:
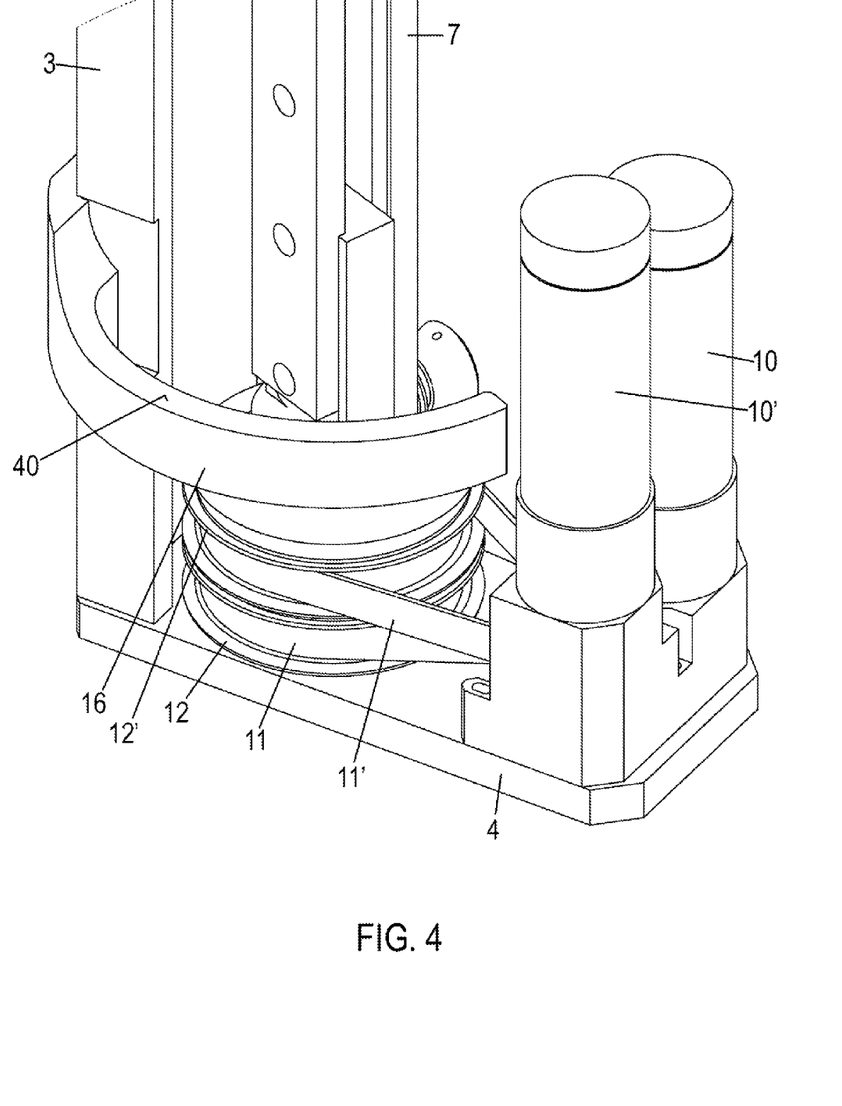
FIG. 4 illustrates an enlarged detail (lower portion) of the device of FIG. 1 according to an embodiment of the present disclosure.
Figure 5:
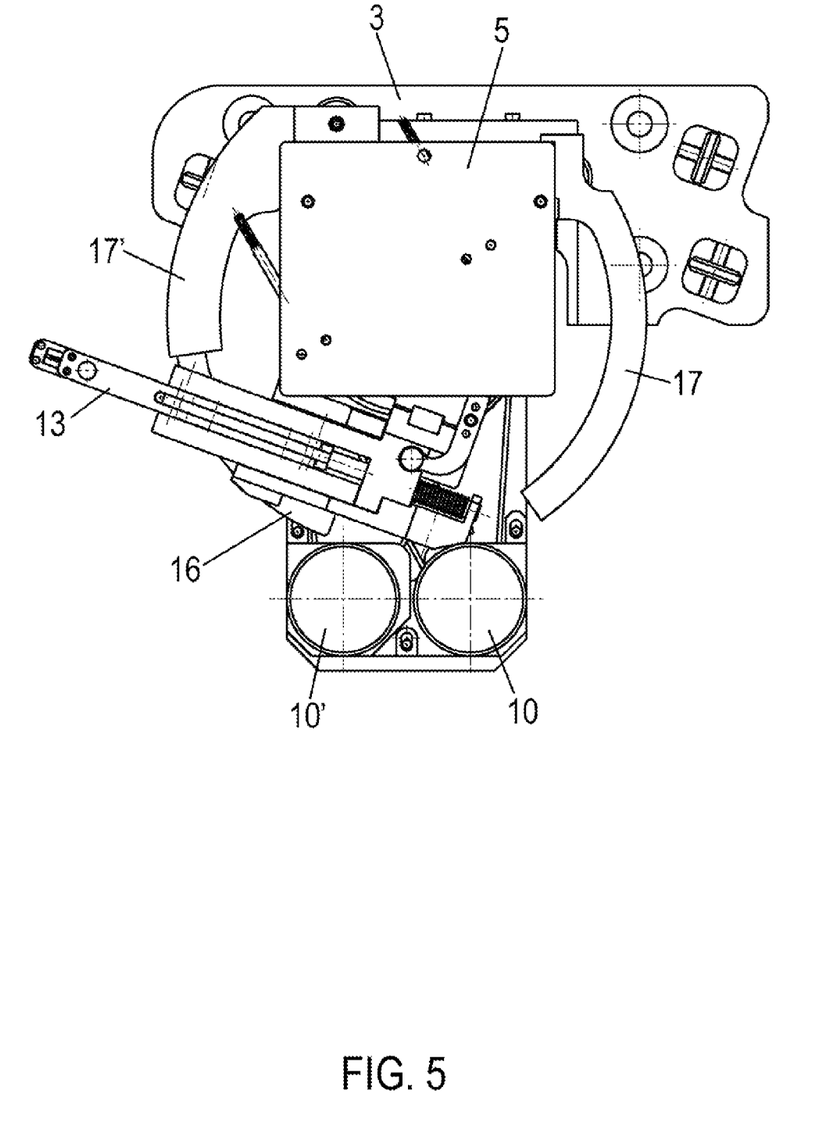
FIG. 5 illustrates a top view of the device of FIG. 1 according to an embodiment of the present disclosure.
Figure 6:
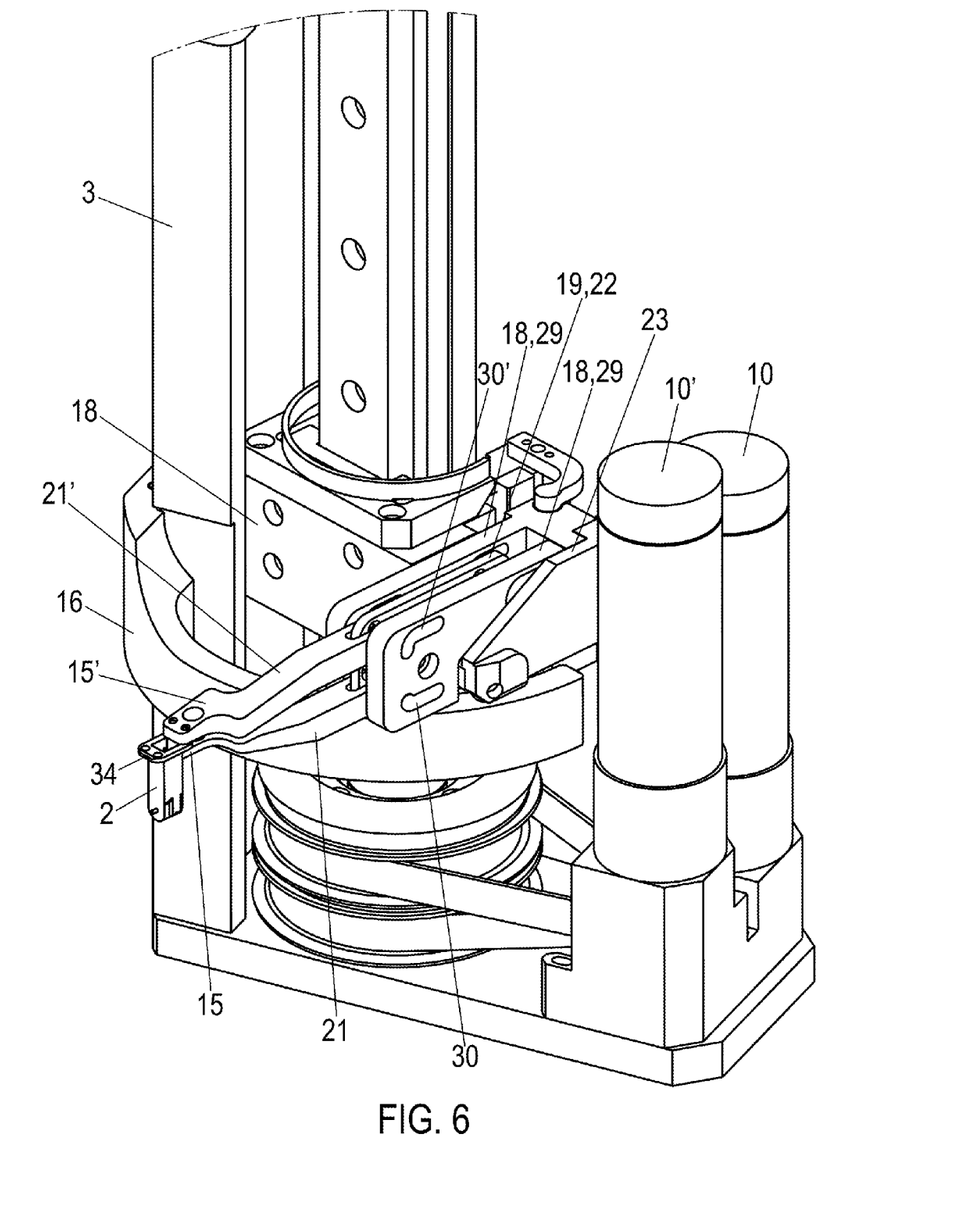
FIG. 6 illustrates an enlarged detail of the device of FIG. 1 comprising the gripper according to an embodiment of the present disclosure.

The device 1 can comprise a gripper 13 provided with two gripping jaws 15, 15' for gripping a vessel 2. As can be seen in FIG. 3, each vessel 2 can comprise a bottom-closed body 32 open on the top for receiving liquid. The body 32 can comprise side walls 33 provided with a flange 34 projecting perpendicularly from the side walls 33 and integrally formed therewith. The upper gripping jaw 15' and the flange 34 can be provided with two pairs of engagement elements, each of which comprise a projection 35 and a depression 36. In one embodiment, the flange 34 can have two depressions 36 and the upper gripping jaw 15' can have two projections 35 for engagement with the depressions 36. Accordingly, the reliability of gripping and holding a vessel 2 can be improved so as to reduce the risk of a failure.

The gripper 13 can be fixed to the support 7 so as to be translatable along the longitudinal axis 8. In one embodiment, the support 7 can be provided with a gripper guide 14 extending along the longitudinal axis 8 of the support 7 in vertical direction for guiding the gripper 13. Accordingly, the gripper 13 can be translated along the gripper guide 14.

A translating mechanism 37 can be coupled to the gripper 13 for translating the gripper 13 along the gripper guide 14. The translating mechanism 37 can be configured as belt drive comprising an electric motor 10' for driving a belt 11'. The belt 11' can be wound around a driving wheel 12' that can be coupled to another belt 11" fixed in translation to the gripper 13. Accordingly, the gripper 13 can be translated along the gripper guide 14 by driving the belt 11" by rotating the wheel 12', with the latter one rotated by the motor-driven belt 11'.

Accordingly, the gripper 13 can be rotated by driving the wheel 12 and can be translated by driving the wheel 12'. Since the electric motors 10, 10' can be independently controlled with respect to each other, the gripper 13 can be rotated or translated or can have a combined translational/rotational movement.

As can, for example, be seen in FIG. 1, the device 1 can further comprise a lower reference element 16 and two upper reference elements 17, 17', each of which can be shaped as a ring segment covering a range of segment angles, for example, between 45° and 180°. It, however, is to be understood that any other range of segment angles can be envisaged according to the specific demands of the user.

The reference elements 16, 17, 17' can be fixed to the mount 3 so as to be stationary with respect to the support 7 and gripper 13, respectively. Each reference element 16, 17, 17' can define a stop position 38, 39, 39' for a vertical movement (translation) of the gripper 13, with the lower reference element 16 defining a lower stop position 38 and the two upper reference elements 17, 17' defining two upper stop positions 39, 39' so that the device 1 can have stop positions in two different heights (positions of the longitudinal axis 8).

The gripping jaws 15, 15' can be passively biasable towards each other to close the gripper 13 for holding a vessel 2 between the stop positions as defined by the reference elements 16, 17, 17' and can be actively biasable away from each other to open the gripper 13 by pushing the gripper 13 against a reference element 16, 17, 17' in a stop position 38, 39, 39'. The gripper 13 can be pushed against one reference element 16, 17, 17' by translating and/or rotating the gripper 13. Due to the vertical orientation of the support 7, the upper reference elements 17, 17' can be in a higher position than the lower reference element 16, with the upper reference elements 17, 17' being on opposite sides of the support 7.

The stop position 38 of the lower reference element 16 can, for example, be located in correspondence to a picking position 103 of the system 100 for picking-up separated vessels 2 provided by an automated separator 101 for separating vessels 2 supplied in bulk form and providing separated vessels 2 at the picking position 103. Thus, the stop positions 39, 39' of the upper reference elements 17, 17' can be located in correspondence to an analytical compartment 102 of the system 100 for releasing or gripping vessels 2, for example, for analyzing samples. Due to the arrangement of the upper reference elements 17, 17', vessels 2 can also be released on opposite sides of the support 7. One stop position of the upper reference elements 17, 17' can, for example, be used for releasing vessels 2 into a waste compartment of the system 100 or into a second analytical compartment.

Figure 2:
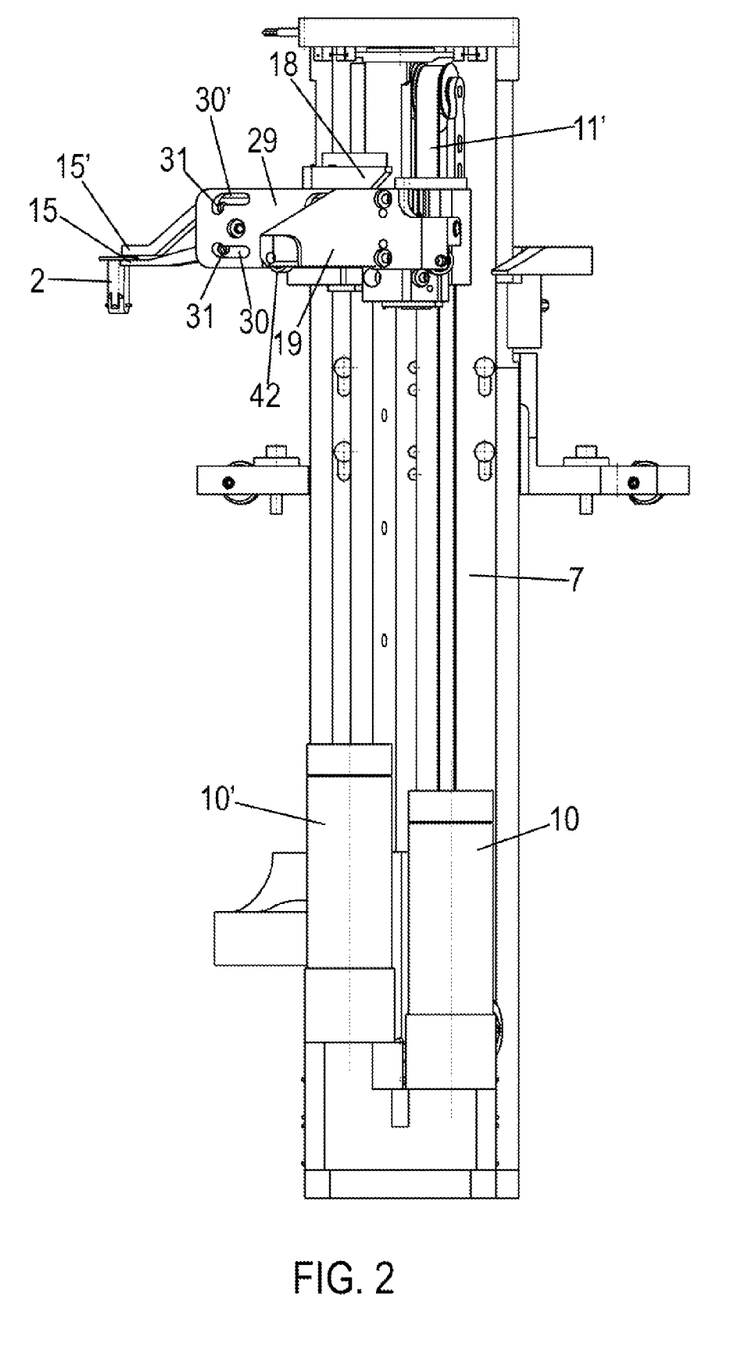
FIG. 2 illustrates a side view of the device of FIG. 1 according to an embodiment of the present disclosure.

Each of the reference elements 16, 17, 17' can have an upper guiding face 40 for guiding the gripper 13. In one embodiment, the guiding face 40 can be configured as sliding face for sliding engagement with the gripper 13. Accordingly, the gripper 13 can be kept open in case of rotating the gripper 13 around the rotational axis 8. As a result, vessels 2 can be taken up or released in a broad range of angles of a stop position 38, 39, 39'. As can be seen in FIG. 2, the gripper base 19 can be provided with a contact wheel 42 for rolling on the guiding face 40 by rotating the gripper 13 around the mount 3. Accordingly, a friction between the gripper 13 and a reference element 16, 17, 17' can advantageously be reduced.

With reference to FIGS. 3 and 5 to 8, the gripper 13 can comprise a gripper head 18 and a gripper base 19. The gripper head 18 can be translatably fixed to the support 7 guidable (guided) by the gripper guide 14. Accordingly, the gripper head 18 can be translated along the gripper guide 14 by driving the translating mechanism 37 as above-described. The gripper head 19 can be movably fixed to the gripper base 18 as to be movable relative to the gripper base 18 against the resilient force of resilient members 20, 20' by pushing the gripper base 19 against a reference element 16, 17, 17'. The gripper base 19 can comprise two gripper legs 21, 21', each of which can be provided with one gripping jaw 15, 15' at an end portion thereof. In one embodiment, the gripper legs 21, 21', for example, can be configured as a lower gripper leg 21 provided with the lower gripping jaw 15 and an upper gripper leg 21' provided with the upper gripping jaw 15' so that the flange 34 of a vessel 2 in an up-right position can readily be gripped.

Figure 7:
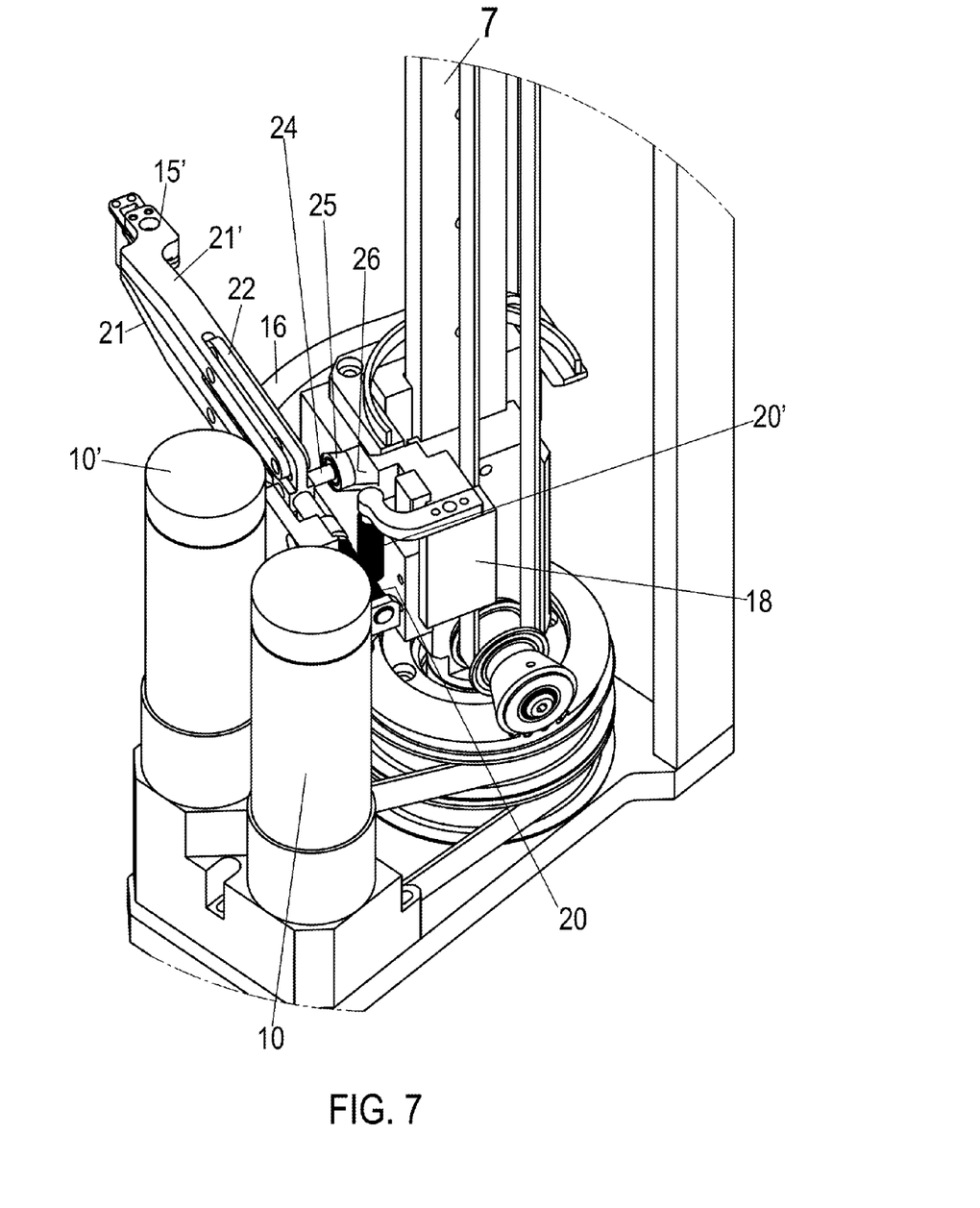
FIG. 7 illustrates another view of the enlarged detail of FIG. 6 according to an embodiment of the present disclosure.
Figure 8:
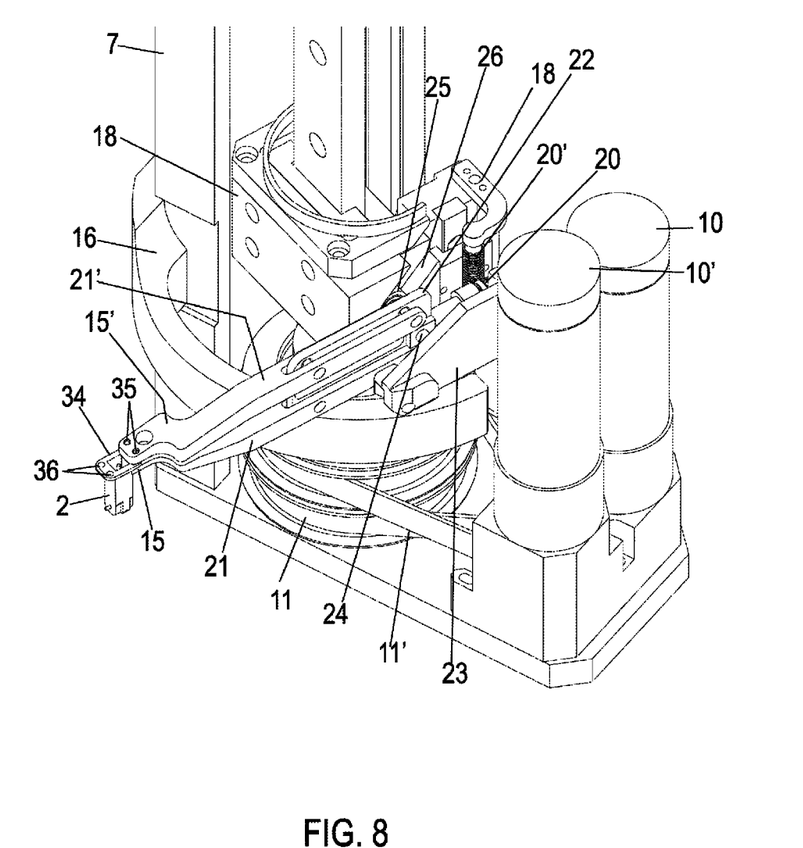
FIG. 8 illustrates a yet another view of the enlarged detail of FIG. 6 according to an embodiment of the present disclosure.

As can be seen in FIGS. 7 and 8, the gripper base 19 can further comprise a leg support 22, for example, configured as a (e.g. vertical) plate-like member for fixing of the gripper legs 21, 21' in a manner that the gripper legs 21, 21' can be movable (moved) together with the leg support 22, with the gripping jaws 15, 15' movable towards and away from each other. A first resilient element 20, such as but not limited to a compression spring, can be arranged between the leg support 22 and a push element 23 which can also be a component of the gripper base 19. The push element 23 can be used to push the gripper base 19 against a reference element 16, 17, 17' in a stop position 38, 39, 39'.

At the distant end of the leg support 22 relative to the gripping jaws 15, 15', the leg support 22 is connected to an elongate guiding link 24, such as but not limited to a connecting rod, which on one side is fixed to the push element 23 and on the other side is provided with a base guiding element 25, such as but not limited to a guiding roller, guidable (guided) by a base guide 26 provided by the gripper head 18. Specifically, as illustrated, the base guide 26 can, e.g., be configured as a linear recess extending inclined with respect to the longitudinal axis 8. Accordingly, in case the push element 23 is pushed against a reference element 16, 17, 17' by translating the gripper 13 (i.e. gripper head 18), the gripper head 18 can be moved relative to the gripper base 19, with the gripping jaws 15, 15' being drawn away guided by the base guide 26 so as to have a component of movement perpendicular to the longitudinal axis 8. Since the gripper legs 21, 21' are fixed to the leg support 22, the gripper legs 21, 21' can be moved together with the leg support 22. A second resilient element 20', such as but not limited to a compression spring, is arranged between the gripper head 18 and the gripper base 19 so as to increase the resilient force when pushing the push element 23 against a reference element 16, 17, 17'. Accordingly, the gripper base 19 (and the gripper legs 21, 21') can be pushed back (reverse movement) by the resilient force of the second resilient force 20' in a position of the gripping jaws 15, 15' other than a stop position 38, 39, 39'.

The gripper head 18 can further comprise two jaw guiding elements 29 arranged on both sides of the gripping legs 21, 21'. The jaw guiding elements 29 can, for example, be configured as plates which, for example, can be vertically arranged in parallel arrangement with the leg support 22. Each of the jaw guiding elements 29 can be provided with two jaw guides 30, 30' arranged above/below of each other in correspondence to the gripper legs 21, 21' for guiding of the gripper legs 21, 21' and gripping jaws 15, 15', respectively. In one embodiment, each jaw guide 30, 30' can be configured as a recess or through-hole formed by the jaw guiding element 29, with a leg nose 31 (see FIG. 2) projecting from each of the gripper legs 21, 21' inserted in the jaw guide 30, 30' for guiding of the gripper leg 21, 21'. Accordingly, the gripper legs 21, 21' can be moved relative to the jaw guiding elements 29 when moving the gripper head 18 relative to the gripper base 19, for example, by pushing the gripper base 19 against a reference element 16, 17, 17' in a stop position 38, 39, 39'.

The jaw guides 30, 30' of each of the jaw guiding elements 29 can be shaped as to move the gripping jaws 15, 15' away from each other by pushing the gripper base 19 against a reference element 16, 17, 17' or to move the gripping jaws 15, 15' towards each other in gripper positions other than the stop positions 38, 39, 39'. Accordingly, by pushing the gripper base 19 and push element 23, respectively, against a reference element 16, 17, 17', the gripper legs 21, 21' can be moved backwards to have a component of movement perpendicular to the longitudinal axis 8 so as to move the gripping jaws 15, 15' away from each other. Furthermore, the gripper legs 21, 21' can be moved forwards (in the reverse direction) by the resilient force of the resilient element 21' so as to move the gripping jaws 15, 15' towards each other. The forward and backward movement of the gripping jaws 15, 15' can advantageously be used for gripping or releasing a vessel 2.

As illustrated in FIG. 1, the device 1 for gripping vessels 2 can be part of a system 100 for analyzing samples, comprising a separator 101 for separating vessels 2 supplied in bulk form and providing single vessels 2 to a picking position 103 and at least one analytical compartment 102 for analyzing samples with the vessels 2. The picking position 103 can be located in correspondence to the stop position 38 of, for example, the lower reference element 16 so as to pick up separated vessels 2 by the gripper 13 by pushing the gripper 13 against the lower reference element 16. Accordingly, the stop position 39, 39' of one of the upper reference elements 17, 17' can be located in correspondence to the analytical compartment 102 so as to release the gripped vessel 2 for using in analyzing samples. One of the stop positions 39, 39' of the upper reference elements 17, 17' can be used to release a gripped vessel 2 into a waste compartment.

Figure 9:
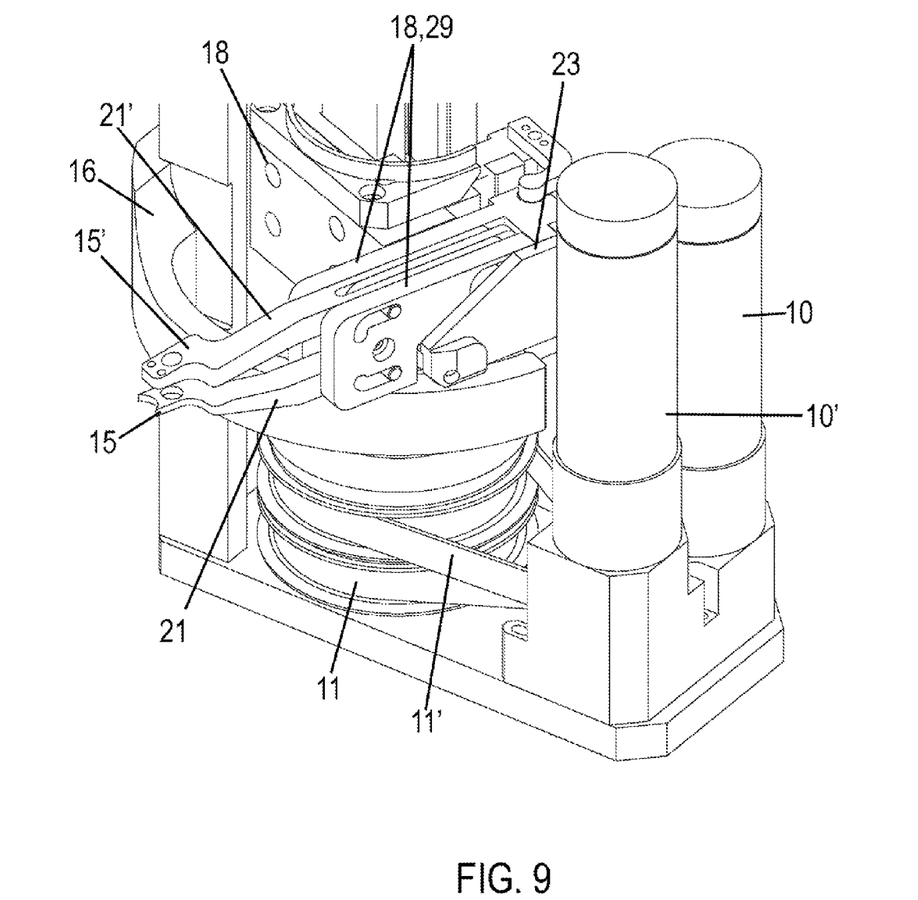
FIG. 9 illustrates a different view of the enlarged detail of FIG. 6 having open gripping

For taking up and releasing a vessel 2, the gripper 13 can be moved to a first stop position 38, 39, 39' as defined by one of the reference elements 16, 17, 17' (for example, the lower reference element 16). The gripper 13 can then be opened by translating the gripper 13 and pushing the push element 23 against a first reference element 16, 17, 17'. The gripper 13 can then be reclosed by translating the gripper 13 away from the first reference element 16, 17, 17' so as to grip the vessel 2. This can be followed by moving the gripper 13 to a second stop position 38, 39, 39' as defined by a second reference element 16, 17, 17' (e.g. one of the upper reference elements 17, 17') and opening the gripper 13 by pushing the push element 23 against the second reference element 16, 17, 17' for releasing the vessel 2. FIG. 9 illustrates the gripper 13 in an open condition in which the gripping jaws 15, 15' are distanced with respect to each other.

A major advantage can be that the gripper 13 (i.e. the gripper base 19) can keep contact with a reference element 16, 17, 17' while opening or closing the gripping jaws 15, 15'. In a stop position 38, 39, 39' in which the gripper base 19 is in contact with a reference element 16, 17, 17', the gripper head 18 can be moved relative to the gripper base 19 in order to open or close the gripping jaws 15, 15', while keeping the gripper base 19 in permanent contact with the reference element 16, 17, 17'. Accordingly, the position of the gripper base 19 relative to the longitudinal axis 8 can remain unchanged when opening or closing the gripping jaws 15, 15'. As a result, a vessel 2 can reliably be gripped or released.

At a same stop position 38, 39, 39', a range of rotational positions of the gripper 13 around the longitudinal axis 8 can be accessible for taking up or releasing vessels 2. The reference element 16, 17, 17' shaped as a ring segment can be used to keep the gripper 13 in an open position while moving the gripper base 19 along the ring segment. As a result, the gripping jaws 15, 15' can be moved sideways in an open position to a position where a vessel 2 can be located, followed by a translation of the gripper head 18 relative to the gripper base 19 so as to close the gripping jaws 15, 15' and grip the vessel 2. By the reverse operation, the vessel 2 can be released.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Obviously, many modifications and variations of the present disclosure are possible in light of the above description. It is therefore to be understood, that within the scope of appended claims, the present disclosure may be practiced otherwise than as specifically devised. For instance, the gripper 13 can be opened by pushing the gripper legs 21, 21' against a reference element 16, 17, 17'. Furthermore, instead of stop positions in two positions relative to the longitudinal axis 8, stop positions in more than two positions relative to the longitudinal axis 8 can be envisaged according to the specific demands of the user. The support 7 can have an orientation than vertical, such as, but not limited to a horizontal orientation. The gripping jaws 15, 15' can be arranged to be movable towards or away from each other in a horizontal direction.

The device 1 of the invention can have many advantages over the prior art. A major advantage can be that the gripping jaws 15, 15' can be operated without a motor and a need to move cables. Instead, the gripping jaws 15, 15' can readily be operated by pushing (e.g. translating) the gripper base 19 against a reference element 16, 17, 17' for opening the gripper 13 and using the resilient force of at least one resilient element 20' for closing the gripper 13 in gripper positions different from the stop positions 38, 39, 39'. Moreover, the device 1 can be highly compact in design resulting in a comparably small foot-print, and can be simple and robust in construction so as to be suitable for long-term maintenance-free usage. Samples can be processed in a highly cost-efficient manner.

We claim:

1. A device for gripping vessels, the device comprising:
a stationary mount;
an elongate support having a longitudinal axis coupled to the mount as to be rotatable relative to the mount around the longitudinal axis;
a rotating mechanism for rotating the support;
a gripper coupled to the support as to be translatable relative to the support along the longitudinal axis, wherein the gripper is provided with gripping jaws for gripping a vessel and comprises,
   a gripper head coupled to the support as to be translatable with respect to the support along the longitudinal axis, and
   a gripper base provided with the gripping jaws, with the gripper head coupled to the gripper base as to be movable relative to the gripper base against the resilient force of at least one resilient member by pushing the gripper base against a reference element in a stop position, wherein the gripping jaws are coupled to the gripper head as to be moved away from each other by pushing the gripper base against a reference element and to be moved towards each other in positions other than the stop positions and wherein the gripper head is coupled to the gripper base as to be movable relative to the gripper base having a component of movement perpendicular to the longitudinal axis of the support configured to move the gripping jaws towards or away from the longitudinal axis while pushing the gripper base against the reference element in order to reach out and grip a vessel;
a translating mechanism for translating the gripper;
a first actuator for driving the rotating mechanism;
a second actuator for driving the translating mechanism; and
at least two reference elements fixed to the mount in at least two different stop positions;

wherein the gripping jaws are passively biasable towards each other for holding a vessel at positions other than the at least two stop positions and wherein the gripping jaws are actively biasable away from each other by pushing the gripper against a reference element in one of the stop positions.

2. The device according to claim 1, wherein the gripper head is provided with a base guide for guiding the gripper base with the base guide inclined with respect to the longitudinal axis of the support.

3. The device according to claim 1, wherein the gripper head is provided with at least one jaw guide coupled to a gripping jaw for guiding the gripping jaw with the jaw guide shaped in a manner to move the gripping jaws away from each other by pushing the gripper base against a reference element and to move the gripping jaws towards each other in positions other than the stop positions.

4. The device according to claim 1, wherein the support is provided with a gripper guide extending along the longitudinal axis for guiding the gripper.

5. The device according to claim 1, wherein at least one reference element is shaped as a ring segment.

6. The device according to claim 1, wherein at least one reference element comprises a guiding face for guiding the gripper along the guiding face by rotating the gripper around the longitudinal axis of the support.

7. The device according to claim 6, wherein the gripper comprises at least one contact wheel for rolling on the guiding face of a reference element by rotating the gripper around the longitudinal axis of the support.

8. The device according to claim 1, wherein the translating mechanism and/or the rotating mechanism is configured as a belt drive.

9. The device according to claim 1, wherein at least one gripping jaw comprises at least one engagement element for engagement with a corresponding engagement element of a vessel.

10. A system for analyzing samples, the system comprising:
    a separator for separating vessels supplied in bulk form and providing separated vessels to a picking position;
    at least one analytical compartment for analyzing samples with the vessels; and
    a device for gripping vessels according to claim 1 for transferring vessels from the picking position located in correspondence to a first stop position to the at least one analytical compartment located in correspondence to at least one second stop position.

11. The system according to claim 10, wherein the device for gripping vessels comprises a third stop position for releasing vessels into a waste compartment or a second analytical compartment.

12. A method for gripping vessels, the method comprising:
    moving a gripper provided with gripping jaws passively biased towards each other to a first stop position;
    opening the gripper by pushing the gripper against a first reference element for taking up a vessel;
    reclosing the gripper by moving the gripper away from the first reference element so as to grip a vessel;
    moving the gripper to a second stop position; and
    opening the gripper by pushing the gripper against a second reference element for releasing the vessel
    wherein the gripper is moved perpendicular to a longitudinal axis of a support to move the gripping jaws towards or away from the longitudinal axis while pushing the gripper base against the reference element in order to reach out and grip a vessel.

13. The method according to claim 12, wherein moving of the gripper comprises translating and/or rotating the gripper.

* * * * *